United States Patent [19]

Dow et al.

[11] Patent Number: 5,036,768
[45] Date of Patent: Aug. 6, 1991

[54] ATTENUATOR FOR DISSIPATING ELECTROMAGNETIC AND ELECTROSTATIC ENERGY

[76] Inventors: Robert L. Dow, Rte. 5, Box 415, LaPlata, Md. 20646; Paul W. Proctor, Rte. 2, Box 60, Kathy La., White Plains, Md. 20695

[21] Appl. No.: 479,117

[22] Filed: Feb. 13, 1990

[51] Int. Cl.$^5$ .................... F42B 3/18; F42B 3/185
[52] U.S. Cl. .................... 102/202.2; 102/202.3
[58] Field of Search ............... 102/202.1, 202.2, 202.3

[56] References Cited

U.S. PATENT DOCUMENTS

| | | | |
|---|---|---|---|
| 2,818,020 | 12/1957 | Burklund | 102/202.2 |
| 4,378,738 | 4/1983 | Proctor et al. | 102/202.7 |
| 4,517,895 | 5/1985 | Rucker | 102/202.2 |
| 4,592,280 | 6/1986 | Shores | 102/202.2 |
| 4,848,233 | 7/1989 | Dow et al. | 102/202.2 |

Primary Examiner—Charles T. Jordan
Attorney, Agent, or Firm—Terry M. Gernstein

[57] ABSTRACT

An attenuator for dissipating electromagnetic energy and equalizing electrostatic energy is formed of a lossy ferrite material having an electrical resistance in a range of about 3,000 to 50,000 ohms. A conductor passes through the material and thence to a bridgewire to supply a firing charge to heat the bridgewire. In one embodiment of the invention, the attenuator is mounted within an electrically and thermally conductive housing, which will dissipate heat and equalize electromagnetic energy which may be induced in the conductor. A capacitive effect may be imparted by the orientation of the conductor as it passes through the ferrite. The capacitive effect is produced in winding the conductor parallel to the metal housing, and parallel to any other conductor passing through the ferrite. In the preferred form, the conductors are wound through the ferrite in a spiral pattern parallel to the conductor housing.

25 Claims, 5 Drawing Sheets

ATTENUATOR FOR DISSIPATING ELECTROMAGNETIC AND ELECTROSTATIC ENERGY

TECHNICAL FIELD

The present invention relates generally to electroexplosive devices (EED's), and more particularly to an apparatus for attenuating broadband electromagnetic radiation and electrostatic current induced in a conductor in an EED.

BACKGROUND OF THE INVENTION

Electroexplosive devices (EED's) such as detonators and blasting caps are sensitive to electromagnetic radiation and electrostatic charges, and can be prematurely or inadvertently detonated by such radiation and charges. Squibs may also be classified as EED's, even though they may contain a pyrotechnic composition instead of an explosive. Regardless of whether a low explosive or a pyrotechnic compositon is used, the composition in the EED is energetic and the function is the same—to begin a very rapid energetic reaction on command.

A typical EED has a fine gauge bridgewire embedded in a chemical mixture that ignites when brought to a high temperature, the bridgewire being heated by passing a relatively small amount of direct current therethrough. Because so little energy is required to ignite an EED, it is very sensitive to high frequency radiation which may be readily induced into the input leads and then into the bridgewire. EED's are also known to be sensitive to transient or spurious signals, stray currents, and static charges.

Various methods have been used to alleviate misfiring caused by electromagnetic radiation. Prior art systems have included RF traps with inductive and capacitive components, ferrite beads and external capacitors, and bypass circuits using diode and capacitor combinations. However, such devices—having a plurality of discrete components—are relatively expensive, and many of the prior RF attenuation systems cannot be readily applied to existing EED's. In addition, prior attenuators have generally been unsuitable for commercial production because of the costs involved in producing the units.

While the applicants herein have successfully created a device which attenuates electromagnetic energy and separates components which provide protection from electrostatic energy, as disclosed in U.S. Pat. No. 4,378,738, several improvements have been made thereto. All previous attempts to protect against stray electrostatic energy have utilized separate specialized components in the EED. Such components add additional cost to the device, and require an additional amount of labor to install them thereon.

Another problem with conventional attenuation devices is in the amount of attenuation provided in proportion to the size of the attenuator. Prior art devices required the serial stacking of a plurality of "beads" (ferrite devices having a single aperture with a single straight longitudinal conductor therethrough), in order to produce the necessary amount of attenuation. The applicants' previous U.S. Pat. No. 4,378,738, helped reduce the overall length of the device by the use of a conductor which passes through the ferrite three times. However, additional attenuation may be desired in many instances where a greater safety margin is necessary, or where a relatively short length requirement limits the use of prior devices.

It is therefore a general object of the present invention to provide an improved broadband ferrite choke attenuator.

Another object of the present invention is to provide a broadband attenuator which will attenuate electromagnetic radiation and equalize electrostatic charges without additional accessory devices.

A further object of the present invention is to provide an attenuation device which provides attenuation power equal to prior art devices, but using a lesser longitudinal length.

Yet another object of the present invention is to provide an attenuator which may be utilized in connection with a variety of different devices.

These and other objects of the present invention will be readily apparent to those skilled in the art.

SUMMARY OF THE INVENTION

The present invention consists of a lossy ferrite attenuator that dissipates spurious electromagnetic energy over a very broadband frequency range, from broadcast to millimeter wavelength frequencies, without resonant or nonattenuating frequencies and converts the dissipated RF energy into heat. The lossy ferrite attenuator simultaneously provides a charge equalization function and grounding effect for induced electrostatic energy and unattenuated RF energy. The lossy ferrite attenuator must have a high Curie temperature so that the attenuator continues dissipating spurious electromagnetic or RF energy even when the conductors leading into the lossy ferrite are exposed to very high electromagnetic fields. Attenuators with electrical resistance between 3,000 and 50,000 ohms have demonstrated that they will effectively equalize spurious electrostatic energy while still passing an effective firing signal through conductors to various electroactivated starter devices. Ferrite attenuators with Curie temperatures of 280° C. and with exposed wire leads have successfully withstood exposures to operating radars without failure. The lowest safe Curie temperature is estimated to be 150° C. Lower Curie temperatures could result in the attenuator failing even when exposed to only moderate RF energy fields.

The lossy ferrite attenuator may be placed inside any of a variety of electroactivated starter devices used primarily in explosive devices in order to increase their operating safety margin and to provide protection against inadvertent actuation. The output of these devices may be explosive, such as electric blasting caps or detonators, or pyrotechnic, such as electric squibs or igniters. Another use is removal of spurious electromagnetic and electrostatic impulses in a fire line by use of an in-line firing line filter. For successful integration into any one of these devices, four conditions must be met.

First, the heat generated when the spurious electromagnetic energy is dissipated by the lossy ferrite must be removed to prevent the lossy ferrite from reaching or exceeding its Curie temperature. Additionally, the heat generated must be safely removed to prevent any explosive component from catching fire or exploding prior to receiving a firing signal.

Second, the ferrite must also be electrically grounded to an electrically conductive housing or case so that any induced electrostatic charge and unattenuated RF or electromagnetic potential can be safely dissipated and- /or equalized to prevent arcing—another form of inadvertent actuation.

The broadband characteristic and attenuation level required of the attenuator must be maintained inside electroactivated starter devices. The attenuator level is achieved by having sufficient conductor length tightly constrained inside of the ferrite to obtain the attenuation level required. The capacitive effect required for broadband, nonresonant attenuation must be obtained by proper design of the conductor geometry inside the lossy ferrite attenuator. Loops, helixes, spirals, substantially parallel conductors, current flowing in substantially parallel or reversing directions in adjacent conductors or between adjacent conductors and housing, are all possible methods of obtaining the capacitive effect required. The capacitive effect may be between a single conductor and the conductive case, commonly called coaxial devices, or between a plurality of conductors and the conductive case.

A Faraday shield must enclose the output side of the lossy ferrite attenuator and protect any ignition devices such as bridgewires. Without this protection the RF energy can bypass the lossy ferrite attenuator and induce enough energy into the output conductors to fire the bridgewire inadvertently.

DESCRIPTION OF THE PREFERRED EMBODIMENT

Figure 1:
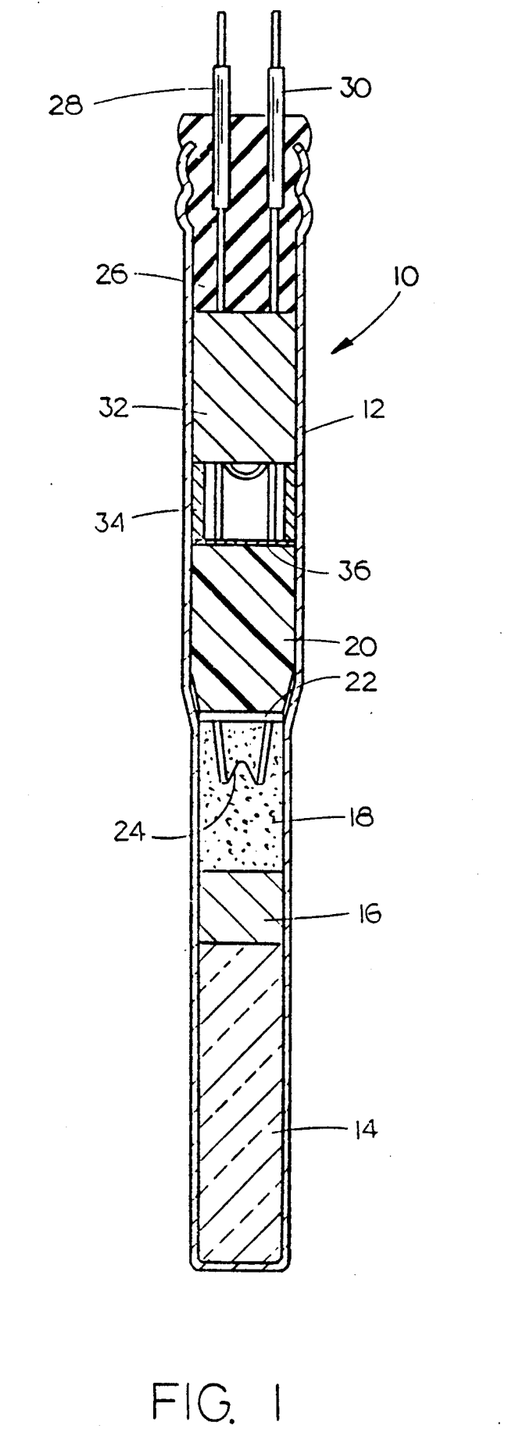
FIG. 1 is a cross-sectional view of a prior art electroexplosive device.

Referring now to the drawings, in which identical or corresponding parts are identified by the same reference character, and more particularly to FIG. 1, an electroexplosive device as known in the prior art is identified generally at 10 and includes a cylindrical metal casing 12 of an electrically conductive material. Although for purposes of illustration the present attenuator is applied to a detonator, it is to be understood that any electroexplosive device may be protected as disclosed herein. The lower portion of casing 12 is typically filled with, in ascending order, a base charge 14, a primer 16 such as lead azide, and an ignition mix 18. The explosive composition formed of 14, 16 and 18 is retained in the lower portion of casing 12 by an electrically insulating polymeric plug 20 having a lower end with an isulating washer 22 mounted thereon. Two conductors passing through plug 20 project out the bottom and into ignition mix 18 to form posts for supporting a bridgewire 24 therebetween. Bridgewire 24 is a fine gauge wire, for example nichrome, that heats up when an electrical current is passed through it. In prior art detonators, the conductors from plug 20 would pass directly to an elastomeric seal 26 at the upper portion of casing 12, where the conductors are insulated, and become input leads 28 and 30. Leads 28 and 30 are coupled to a source of DC power that supplies the firing signal to the electroexplosive device 10.

The applicants herein improved on prior art detonators, by providing a special ferrite attenuator core 32 to attenuate electromagnetic radiation. In the applicants' previous patent, U.S. Pat. No. 4,378,738, an attenuator was described with a conductor which passes longitudinally through attenuator 32 and is coupled to one of the input leads 28, 30. The ferrite attenuator 32 was held in position by a ferrule 34 which also served to space the attenuator 32 from the plug 20, to allow for greater separation and protection of the explosive mixture from the heat generated during attenuation of electromagnetic radiation.

As is known in the art, ferrite is a ceramic semi-conductive material formed of several metallic oxides, such as manganese zinc ferrite, nickel zinc ferrite, magnesium zinc ferrite, and others using bivalent or trivalent substitutions of copper, aluminum, cobalt, lithium and other metals. While the prior art attenuators, such as shown in FIG. 1, were excellent for broadband attenuation of RF energy, the ferrite composition was of an electrically nonconductive character, or treated externally to make the surfaces nonconductive. Thus, the conductors were electrically insulated by the ferrite attenuator 32 from metal casing 12. In some cases, insulated wires were placed through the ferrite attenuator to achieve this insulating function.

Electrostatic protection was previously provided by a short section of a printed circuit tape 36, which electrostatically grounded the conductors to casing 12 when plug 20 was inserted therein. Printed circuit tape 36 acted as a capacitor to shunt any electrostatic charge to casing 12, thus bypassing bridgewire 24.

Figure 2:
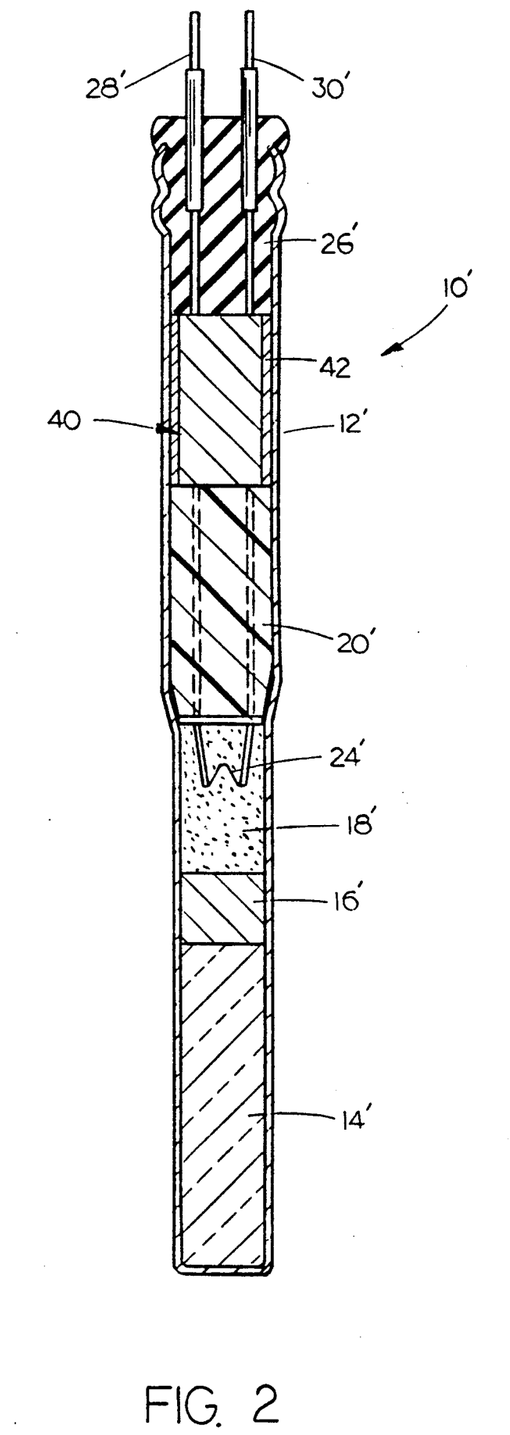
FIG. 2 is a cross-sectional view of an electroexplosive device incorporating an attenuator according to the present invention.

Referring now to FIG. 2, an electroexplosive device 10' includes a metal casing 12', explosive composition formed of 14', 16' and 18', an electrically insulating polymeric plug 20', bridgewire 24', elastomeric seal 26' and a pair of input conductors 28' and 30'. The attenuator of the present invention is designated generally at 40 and is located between plug 20' and elastomeric seal 26'. One of the major improvements in electroexplosive device 10' over the prior art is in the use of a ferrite with different physical properties for attenuator 40. As with past compositions of ferrite, the principal requirements for the ferrite are that it exhibit a broadband attenuation of RF energy from broadcast (meter wavelength) to radar (millimeter wavelength) frequencies, and that it have a high Curie temperature, preferably in excess of about 150° C. (350° F.). The major difference between the improved ferrite composition of the present invention and the ferrite composition of prior art devices, is in the electrical conductivity characteristics of the ferrite, which eliminates the need for previously required discrete parts.

Prior to the present invention, it was believed that the ferrite composition must be electrically nonconductive. The electrical resistance function of the ferrite attenuators of prior art devices was achieved in one of three ways: (1) use of a high electrical-resistance ferrite; (2) use of insulated wires to run through the ferrite; or (3) depositing an insulating coating on the ferrite to achieve the value of electrical insulation required. The applicants herein have discovered that the ferrite composition should *not* be non-conductive, but rather, should have a certain amount of electrical conductivity. This eliminates the need to insulate wires and eliminates the potential failure modes of the insulating coating wearing down during vibration, breaking off due to aging, or wearing out thus simplifying the design, eliminating parts, and lowering cost. In experiments with compositions of ferrite having various electrical resistance values, the inventors have found that a ferrite composition having a "intermediate electrical resistance" will provide electrostatic protection to the attenuator without having to utilize accessory devices. The preferred range of resistance of the ferrite is in the range of 3,000 to 10,000 ohms, with the optimal resistance being about 3800 ohms. Resistance less than 3,000 ohms can affect the reliability of the EED, by shunting a significant fraction of the detonating energy to the casing rather than allowing it to pass to the bridgewire. Theoretically, resistance in the range of 10,000 to 50,000 ohms would be sufficient to provide the resistance necessary to electrostatically protect the device. However, the inventors have not been able to specifically test the performance of compositions of this characteristic.

Another feature of the detonator 10' which differs from the prior devices, is in the use of a thermally and electrically conductive coating 42 between the attenuator 40 and casing 12'. One example of a coating 42 which will work for this purpose is a silicon grease. The coating 42 allows the heat to be conducted to the metal housing 12' in a much more efficient manner. While prior art detonators sometimes utilized coatings for heat transfer purposes, these polymers were electrically insulating. Thus, prior art polymers would allow eletrostatic and RF buildup, creating potential safety hazards because the outer case was not grounded. Also, polymers used in prior art devices were found to provide sufficient clearance between the components and casing of the detonator to allow sneak RF circuits to appear in production units.

The present invention simultaneously provides heat dissipation while electrically grounding the ferrite choke attenuator 40' to outside case 12'. Four methods for constructing the device have been found to be acceptable for attaining these two properties. First, the ferrite choke 40' may be press-fit into outer case 12' to obtain direct and intimate contact therebetween. A second method would utilize a conductive silicone grease, or similar electrically and thermally conductive material, coated on the ferrite choke 40' prior to pressing into casing 12'. The coating reduces friction during insertion and then hardens to form a thermal and electrical conductor. A third method is to pot the ferrite choke into the casing using a thermosetting polymer that is electrically and thermally conductive. Finally, the entire subassembly of FIG. 4, with its own conductive outer metal casing may be pressed into an additional outer casing.

Figure 3:
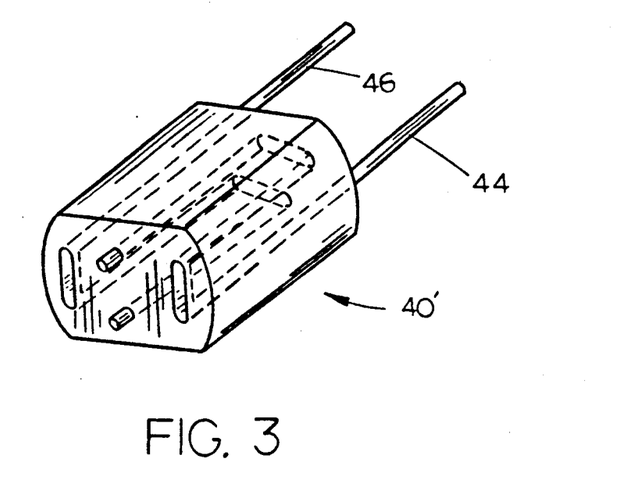
FIG. 3 is a perspective view of the bottom portion of a wired ferrite attenuator.
Figure 4:
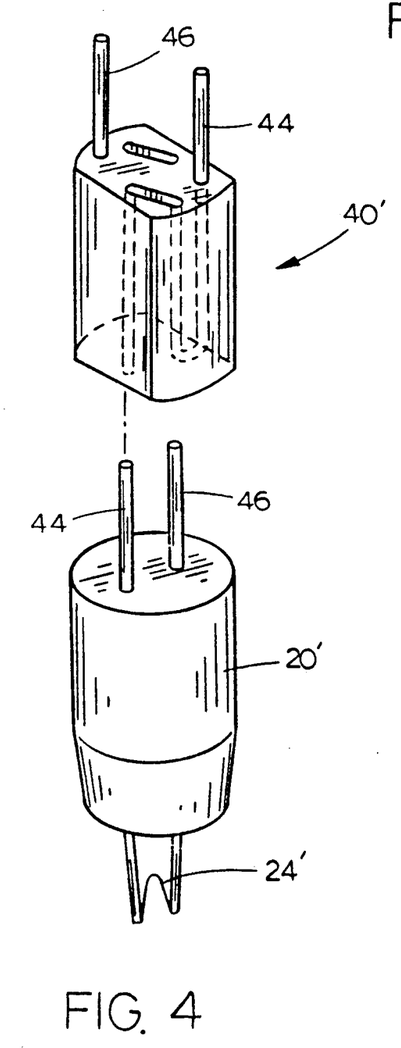
FIG. 4 is an exploded perspective view of the top portion of the ferrite attenuator of FIG. 2, with the attenuator separated from the phenolic plug.

Referring now to FIGS. 3 and 4, a second embodiment of the ferrite attenuator 40' of the present invention is shown with a pair of conductors 44 and 46 wound therethrough. As discussed in the applicants' previous patent, each conductor 44 and 46 extends longitudinally through attenuator 40' and are looped to pass completely through the attenuator three times, and is thereby "wound" longitudinally. This was accomplished in a three-step process: (1) forming the attenuator, (2) forming six longitudinal apertures through the attenuator, and (3) introducing conductors 44 and 46 through the apertures in the attenuator.

This process may be simplified by forming a fused, electrically-conductive pathway through the ferrite attenuator during formation of the attenuator itself. In this manner, the steps of forming apertures and inserting conductors would be eliminated. The process of forming a fused electrical pathway in a ferrite composition is known in the art and will not be described in detail herein. Methods for joining the fused conductive pathway to solid conductors are also known, but will not be described herein.

It has been determined that the critical factor in determining the amount of attenuation of an attenuator is in the length of the conductor which passes through the attenuator. Thus, the effective attenuating power of the attenuator of FIG. 4, each conductor making three passes completely through the attenuator, is three times more than that of the single-pass attenuators of the prior art. The level of attenuation required for each application of the device can therefore be tailored by selecting the path length through the attenuator, a feature previously unavailable.

Figure 5:
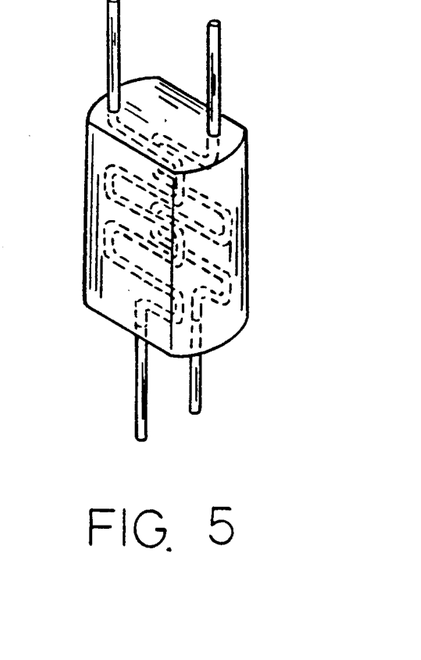
FIG. 5 is a perspective view of a second embodiment of a ferrite attenuator.

It has also been discovered that "winding patterns" other than longitudinal windings previously described, can work equally well. FIG. 5 shows one embodiment of a reversing conductor, capacitive inducing winding in the horizontal plane. This device can be produced in two layers and pressed together before fusing into the ferrite choke attenuator. The reversing conductor design phases the RF energy, greatly improving the attenuation level attainable, shortening the length and enhancing the capacitive effects.

Figure 6:
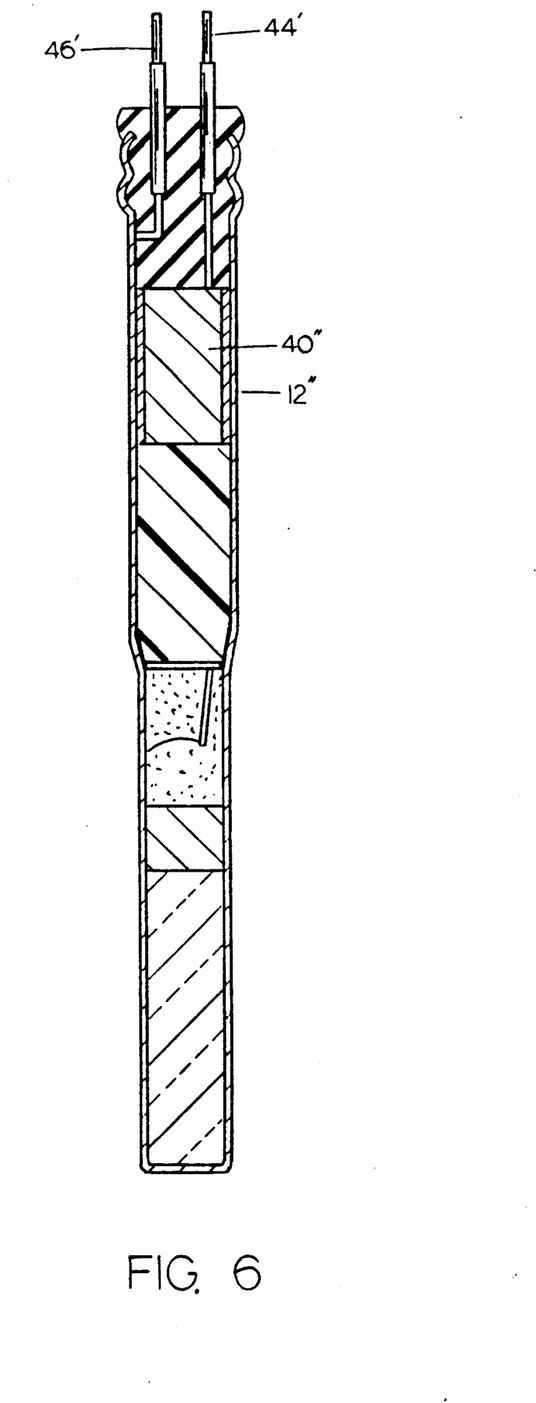
FIG. 6 is a cross-sectional view of an electroexplosive device utilizing a single wire attenuator.
Figure 7:
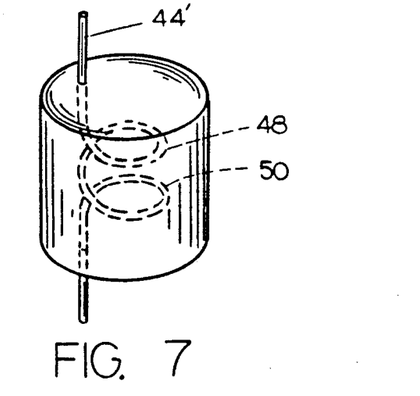
FIG. 7 is a perspective view of a third embodiment of the attenuator of this invention.
Figure 8:
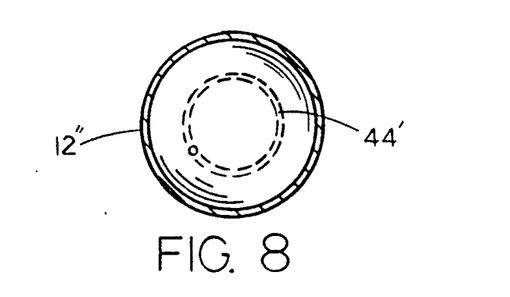
FIG. 8 is a top view of the attenuator of FIG. 7.
Figure 9:
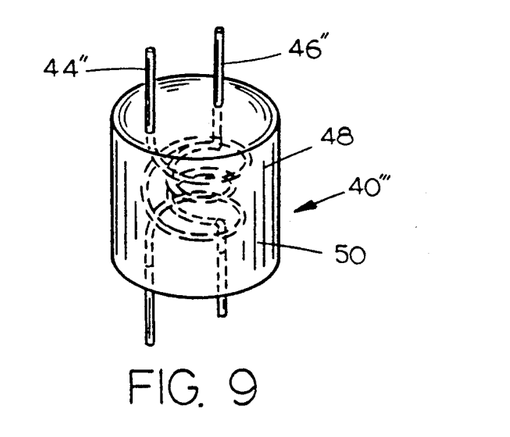
FIG. 9 is a perspective view of a fourth embodiment of an attenuator of the present invention.
Figure 10:
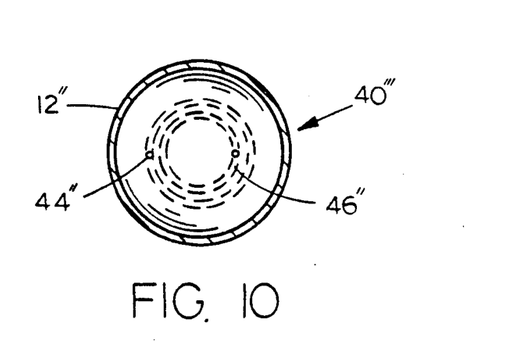
FIG. 10 is a top view of a attenuator of FIG. 9.

FIGS. 6-8 disclose a single conductor attenuator utilizing another new winding pattern of the present invention. In particular, FIGS. 7 and 8 disclose a single conductor attenuator 40" with a single conductor 44' spiraling through the material in a longitudinal direction. The top view of FIG. 8 shows that conductor 44' follows a path concentric to casing 12" and spiraling from the top to the bottom in two "winds" 48 and 50. The length of each wind 48 and 50 is approximately equal to one longitudinal pass of a conductor through the length of the attenuator 40", such that the two-wind attenuator 40" would be twice as effective in attenuation as the prior art single pass "beads". FIGS. 9 and 10 show a dual-conductor attenuator 40'" having a pair of conductors 44" and 46" spiraled therethrough in concentric paths (when viewed from above and in the same horizontal plane through any given radius of the attenuator).

Another critical feature of the new method of winding a attenuator in a spiral, is in winding the conductor parallel to the casing 12" (in the case of a single conductor attenuator 40") as well as parallel between the conductors (in the case of a dual-conductor attenuator 40'"). The parallel orientation of the conductors with each other and the casing produces a capacitive effect which eliminates the need for a separate capacitor. It can also be seen that attenuators utilizing a multiplewind spiral-wound conductor must be formed with a fused conductor pathway since a spiral aperture would be difficult to produce. A "single-wind" spiral can be produced without necessarily resorting to a fused conductor pathway.

While attenuators 40" and 40"' show only two winds 48 and 50 in the conductors, the inventors have found that any number of winds are possible within the attenuator as long as the distance between the conductors is sufficient to eliminate shorting between the conductors and/or between the housing and conductors. The amount of ferrite between the conductors and between the conductors and housing has no direct relation to the attenuation power of the attenuator, and thus need only be as thick as required to keep the ferrite attenuator from disintegrating.

Figure 11:
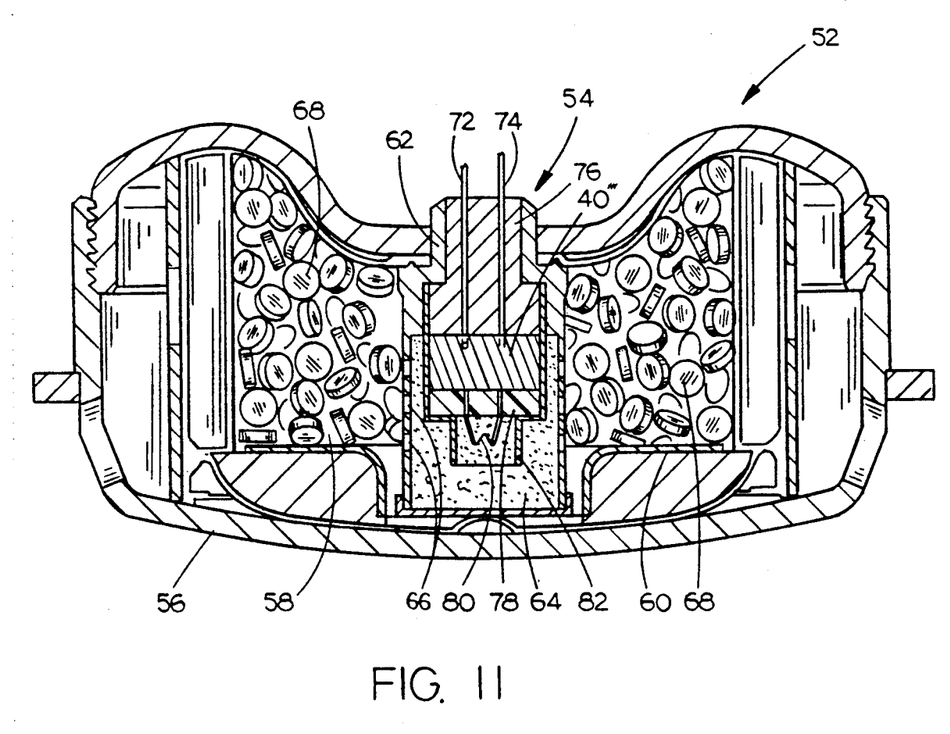
FIG. 11 is a cross-sectional view of an airbag gas generator with a squib utilizing the attenuator shown in FIGS. 8-9.

Referring now to FIG. 11, a conventional airbag gas generator 52 is commonly used to inflate airbag safety devices in vehicles. The ignitor 54 is mounted within a housing 56 which contains a gas generant system 58 typically hermetically sealed within an aluminum cartridge 60. Ignitor 54 includes an electrically conductive metal casing 62 (which provides a heat sink and thermally conductive path) having a pyrotechnic material 64 within one end thereof. A series of apertures 66 in casing 62 allows a high temperature, high pressure charge to escape and ignite the pelletized solid propellant 68 of the gas generant system.

A pair of conductors 72 and 74 extend through an elastomeric plug 76, thence through ferrite attenuator 40"', through polymeric plug 78 and into pyrotechnic material 64, as shown in the drawings. A bridgewire 80 is utilized to ignite the pyrotechnic material 64. An additional interior housing 82 of an electrically conductive metal, extends from casing 62 around attenuator 40"', plug 78 and bridgewires 80. Attenuator 40"' is in intimate electrical and thermal contact with interior housing 82 so as to dissipate heat and electrostatic energy during attenuation of radiation and electrostatic charges. Interior housing 82 also provides a complete Faraday shield to prevent leakage of electromagnetic energy around the ferrite.

In can be seen that the length of attenuator 40"' is a critical factor in uses such as squibs 52, and thus the utilization of a spiral winding of conductors 72 and 74 can be critical to provide the maximum amount of attenuation with the minimal amount of attenuator length.

Figure 12:
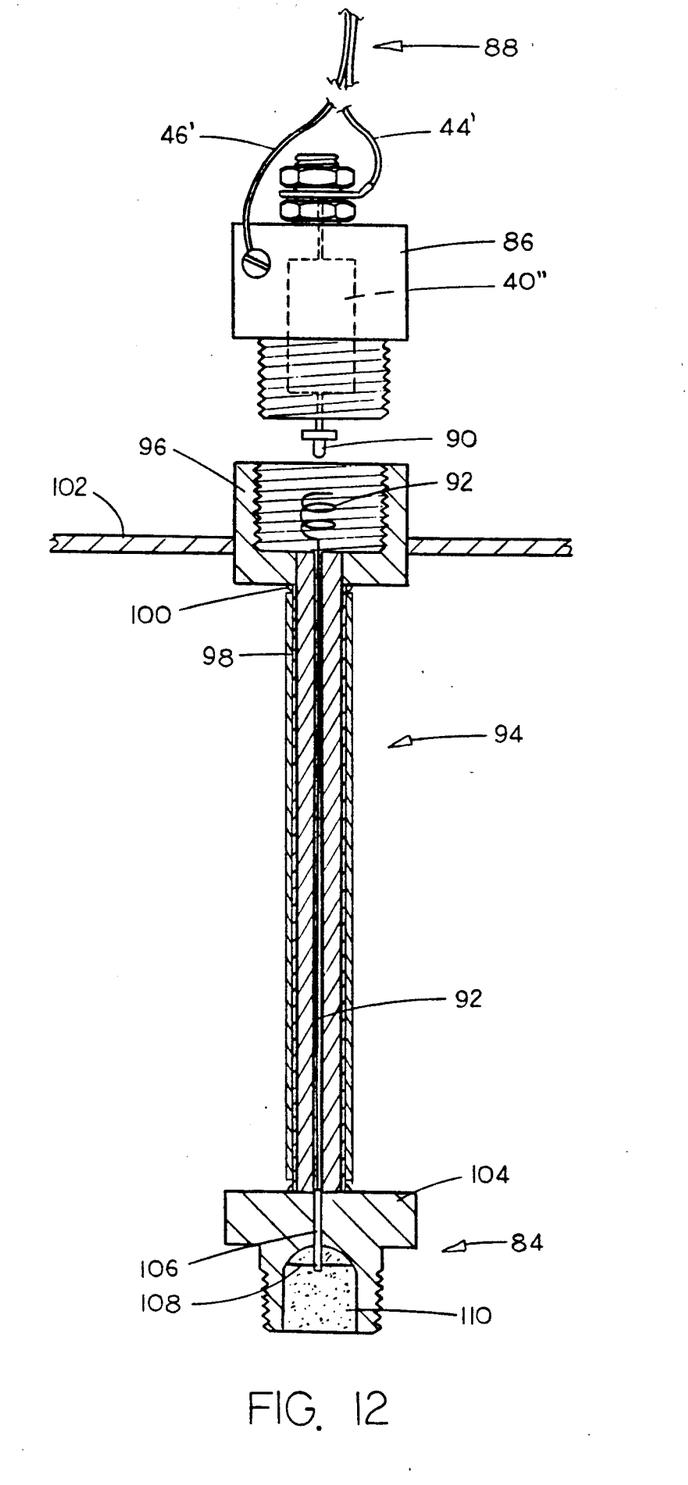
FIG. 12 is a cross-sectional view of a firing line filter with the present invention.

Referring now to FIG. 12, an example is shown of an arrangement with the attenuator 40" located a distance from a squib 84, which allows easy replacement of either squib 84 or attenuator 40" as necessary. This arrangement, which shows functional features similar to the embodiment of FIG. 6, utilizes a single conductor 44' electrically connected to attenuator 40" mounted within a threaded case 86. The second conductor 46" extends from the firing line 88 and is electrically connected to casing 86. The output end of conductor 44' is electrically connected to a pin 90 extending out of attenuator 40" and electrically connected to the center electrode 92 of a coaxial cable 94. Upon threading of case 86 into a receiving case 96, conductor 46' will be electrically connected to the metal sheath 98 of coaxial cable 94. Preferably, sheath 98 is soldered at 100 to case 96 to maintain good electrical connection therewith. Case 96 is mounted to a frame 102 so as to ground the case 96 and conductor 46'.

Coaxial cable 94 may then extend from the fixed case 96 to the squib 84, allowing great latitude in placement of the squib. The metal sheath 98 of coaxial cable 94 shields electrode 92 from electromagnetic radiation. A coaxial squib 84 is connected to coaxial cable 94 with the housing 104 of squib 84 being electrically connected to sheath 98. Electrode 92 is electrically connected to center post 106 of squib 84, which leads to the bridgewire 108. A pyrotechnic mix 110 within squib 84 may then be heated and fired as required.

Whereas the invention has been shown and described in connection with the preferred embodiments thereof, it will be understood that many modifications, substitutions and additions may be made which are within the intended broad scope of the appended claims. For example, the attenuator may be utilized in a variety of different electrical devices in any situation where attenuation of electromagnetic and/or electrostatic energy is required. Thus, the attenuator has the capability of use in computer equipment, and many other devices. It can therefore be seen that the present invetnion fulfills at least all of the above stated objectives.

I claim:

1. A broad band attenuator for attenuating electromagnetic energy and equalizing electrostatic energy induced in a conductor, the attenuator being formed of a lossy ferrite material having a Curie temperature greater than about 150° C. such that electromagnetic energy induced in a conductive pathway through said attenuator will be dissipated as heat in said ferrite, said ferrite material having an electrical conductivity great enough that electrostatic energy induced in a conductive pathway through said attenuator will be shunted through said ferrite to a ground electrically connected to the ferrite, said ferrite material having an electrical resistance great enough to prevent a substantial portion of an electrical firing signal in said conductive pathway from being shunted to ground.

2. The attenuator of claim 1, wherein said ferrite material has an electrical resistance in a range of about 3,000 to 50,000 ohms.

3. The attenuator of claim 2, wherein said ferrite material has an electrical resistance in a range of about 3,000 to 10,000 ohms.

4. The attenuator of claim 3, wherein said ferrite material has an electrical resistance of about 3,800 ohms.

5. In combination:
at least two electrical conductor means for carrying an electrical firing signal from an electrical source to a firing means;
said conductor means passing through an attenuator means for attenuating electromagnetic energy and equalizing electrostatic energy;
said attenuator means being mounted within at least a portion of an electrically and thermally conductive housing, and in contact therewith so as to dissipate heat and electrostatic charges to said housing;
said attenuator means being formed of a lossy ferrite material having a Curie temperature greater than about 150° C., such that electromagnetic energy induced in said conductor means will be dissipated as heat in said ferrite material, said ferrite material having an electrical conductivity great enough that electrostatic energy induced in said electrical conductor means will be shunted through said ferrite to a ground electrically connected to the ferrite, said ferrite material having an electrical resistance great enough to prevent a substantial portion of an electrical firing signal in said conductor means from being shunted to ground;

said housing being formed of a material which will prevent the passage of electromagnetic energy therethrough;

a firing means having an input end electrically connected to said conductor means which is responsive to said firing signal;

said housing enclosing said attenuator means and extending to the input end of said firing means, to shield said conductor means from said attenuator to said firing means;

whereby electromagnetic and electrostatic energy is dissipated by said attenuator, but an electrical firing signal is allowed to pass along said conductor means; and whereby potential of electromagnetic and electrostatic induced energy levels are equalized by said attenuator means.

6. The attenuator of claim 5, wherein said ferrite material has an electrical resistance in a range of about 3,000 to 50,000 ohms.

7. The attenuator of claim 6, wherein said ferrite material has an electrical resistance in a range of about 3,000 to 10,000 ohms.

8. The attenuator of claim 7, wherein said ferrite material has an electrical resistance of about 3,800 ohms.

9. In combination:

at least one electrical conductor means for carrying an electrical firing signal from an electrical source to a firing means;

said conductor means passing through an attenuator means for attenuating electromagnetic energy and equalizing electrostatic energy;

said attenuator means being mounted within at least a portion of a generally cylindrical housing having a top and bottom, said attenuator means being in contact with said housing so as to dissipate thermal energy;

said attenuator means being formed of a lossy ferrite material having a Curie temperature greater than about 150° C., such that electromagnetic energy induced in said conductor means will be dissipated as heat in said ferrite material, said ferrite material having an electrical conductivity great enough that electrostatic energy induced in said electrical conductor means will be shunted through said ferrite to a ground electrically connected to the ferrite, said ferrite material having an electrical resistance great enough to prevent a substantial portion of an electrical firing signal in said conductor means from being shunted to ground;

said housing being formed of a material which will prevent the passage of electromagnetic energy therethrough;

a firing means having an input end electrically connected to said conductor means which is responsive to said electrical firing signal;

said housing enclosing said attenuator means and extending to the input end of said firing means, to shield said conductor means from said attenuator to said firing means; and said conductor means being formed in spiral form within said attenuator and within said housing, said conductor means formed in a three-dimensional curving path from top to bottom in said attenuator, the conductor located a generally constant distance from the longitudinal axis of said housing, so as to provide a capacitative effect between said housing and said conductor means.

10. The combination of claim 9, wherein each rotation of the conductor's curving path around the longitudinal axis of said housing constitutes one wind, and wherein said conductor is of a length to form at least two winds within said attenuator, the paths of each wind being parallel to produce a capacitative effect.

11. In combination:

first and second electrical conductor means for carrying an electrical firing signal from an electrical source to a firing means;

said conductor means passing through an attenuator means for attenuating electromagnetic energy and equalizing electrostatic energy;

said attenuator means being mounted within at least a portion of an electrically and thermally conductive housing having a top and a bottom, said attenuator means being in contact with said housing so as to dissipate thermal energy;

said attenuator means being formed of a lossy ferrite material having a Curie temperature greater than about 150° C., such that said attenuator will dissipate electromagnetic energy induced in said conductor;

said housing being formed of a material which will prevent the passage of electromagnetic energy therethrough;

a firing means having an input end electrically connected to said conductor means which is responsive to said electrical firing signal;

said housing enclosing said attenuator means and extending to the input end of said firing means, to shield said conductor means from said attenuator to said firing means; and said first conductor means being formed in a spiral form within said attenuator and within said housing, said conductor means formed in a three-dimensional curving path from top to bottom in said attenuator;

said second conductor means passing through said attenuator means and formed in a three dimensional spiral concentric to the first conductor means, such that said first and second conductors produce a capacitative effect between themselves.

12. In combination:

at least one electrical conductor means for carrying an electrical firing signal from an electrical source to a firing means;

said conductor means passing through an attenuator means for attenuating electromagnetic energy and equalizing electrostatic energy;

said attenuator means being mounted within at least a portion of a generally cylindrical housing having a top and bottom, said attenuator means being in contact with said housing so as to dissipate thermal energy;

said attenuator means being formed of a lossy ferrite material having a Curie temperature greater than about 150° C., such that electromagnetic energy induced in said conductor means will be dissipated as heat in said ferrite material, said ferrite material having an electrical conductivity great enough that electrostatic energy induced in said conductor means will be shunted through said ferrite to a ground electrically connected to the ferrite, said ferrite material having an electrical resistance great enough to prevent a substantial portion of an electrical firing signal in said conductor means from being shunted to ground;

said housing being formed of a material which will prevent the passage of electromagnetic energy therethrough;

a firing means having an input end electrically connected to said conductor means which is responsive to said electrical firing signal;

said housing enclosing said attenuator means and extending to the input end of said firing means, to shield said conductor means from said attenuator to said firing means; and said conductor means being formed within said attenuator and within said housing with a plurality of portions parallel to one another so as to provide a capacitative effect in said conductor means between said parallel portions.

13. The combination of claim 12, wherein said parallel portions are oriented generally transversely to the longitudinal axis of said attenuator means.

14. The combination of claim 12, further comprising a second conductor passing through said attenuator means and formed with a plurality of portions parallel to one another and parallel to said parallel portions at said first conductor, so as to provide a capacitative effect in said conductor means between said parallel portions of said first and second conductors.

15. A squib, comprising:
a pyrotechnic charge;
electrical means for igniting said pyrotechnic charge, said electrical means including a pair of conductors extending between an electrical source and said pyrotechnic charge;
attenuator means for dissipating electromagnetic energy and equalizing electrostatic energy induced in said conductors, comprising lossy ferrite material within an electrically and thermally conductive housing, said housing surrounding said attenuator and extending to said pyrotechnic charge;
said housing being formed of a material which will prevent the passage of electromagnetic energy therethrough;
said conductors passing through said ferrite material and terminating in said pyrotechnic charge;
an ignitor means electrically connected between said conductors to ignite said pyrotechnic charge upon passage of a firing signal therethrough; and
said ferrite material having a Curie temperature greater than about 150° C. and having an electrical resistance of about 3,000 to 50,000 ohms, whereby electromagnetic energy induced in said conductors is dissipated in said ferrite material, and whereby electrostatic energy induced in said conductors is shunted through said ferrite material to said casing.

16. A broad band attenuator for attenuating electromagnetic energy and equalizing electrostatic energy, the attenuator including a conductive means and a ground element and being formed of a lossy ferrite material in electrical and heat transfering contact with said ground element and with said conductive means and having heat transfer properties such that electromagnetic energy induced in said conductive means will be transferred to said ground element and dissipated as heat, said ferrite material having an electrical conductivity great enough that electrostatic energy induced in said conductive means will be shunted through ferrite material to said ground element, said ferrite material having an electrical resistance great enough to prevent a substantial portion of an electrical firing signal in said conductive means from being shunted to said ground element.

17. A broad band attenuator for attenuating electromagnetic energy and equalizing electrostatic energy comprising:
an electrical ground element;
an electrically conductive means having an electrical resistance;
an electrically conductive ferrite material in electrical contact with said ground element and in electrical contact with said electrically conductive means, said ferrite material further having an electrical conductivity great enough that electrostatic energy induced in said electrically conductive means will be shunted through said ferrite material to said ground element, said ferrite material also having an electrical resistance greater than said electrical conductive means electrical resistance to prevent an electrical firing signal in said electrically conductive means from being shunted to said ground element through said ferrite material.

18. In combination:
at least two electrical conductor means for carrying an electrical firing signal from an electrical source to a firing means;
said conductor means passing through an attenuator means for attenuating electromagnetic energy and equalizing electrostatic energy;
said attenuator means being mounted within at least a portion of an electrically and thermally conductive housing, and in contact therewith so as to dissipate heat and electrostatic charges to said housing;
said attenuator means including an electrical ground element and being formed of an electrically conductive ferrite material in electrical contact with said ground element, said electrical conductor means being in electrical contact with said ferrite material, said ferrite material further having an electrical conductivity great enough that electrostatic energy induced in said electrical conductor means will be shunted through said ferrite material to said ground element, said ferrite material also having an electrical resistance great enough to prevent an electrical firing signal in said conductor means from being shunted to said ground element through said ferrite material;
said housing being formed of a material which will prevent the passage of electromagnetic energy therethrough;
a firing means having an input end electrically connected to said conductor means which is responsive to said firing signal;
said housing enclosing said attenuator means and extending to the input end of said firing means, to shield said conductor means from said attenuator to said firing means;
whereby electromagnetic and electrostatic energy are dissipated by said attenuator, but an electrical firing signal is allowed to pass along said conductor means; and
whereby potential of electromagnetic and electrostatic induced energy levels are equalized by said attenuator means.

19. In combination:

at least one electrical conductor means for carrying an electrical firing signal from an electrical source to a firing means;

said conductor means passing through an attenuator means for attenuating electromagnetic energy and equalizing electrostatic energy;

said attenuator means being mounted within at least a portion of a generally cylindrical housing having a top and bottom, said attenuator means being in contact with said housing so as to dissipate thermal energy;

said attenuator means including an electrical ground element and being formed of an electrically conductive ferrite material in electrical contact with said ground element, said conductor means being in electrical contact with said ferrite material, said ferrite material further having an electrical conductivity great enough that electrostatic energy induced in said electrical conductor means will be shunted through said ferrite material to said ground element, said ferrite material also having an electrical resistance great enough to prevent an electrical firing signal in said conductor means from being shunted to said ground element through said ferrite material;

said housing being formed of a material which will prevent the passage of electromagnetic energy therethrough;

a firing means having an input end electrically connected to said conductor means which is responsive to said electrical firing signal;

said housing enclosing said attenuator means and extending to the input end of said firing means, to shield said conductor means from said attenuator to said firing means; and said conductor means being formed in a spiral form within said attenuator and within said housing, said conductor means formed in a three-dimensional curving path from top to bottom in said attenuator, the conductor located a generally constant distance from the longitudinal axis of said housing, so as to provide a capacitative effect between said housing and said conductor means.

20. The combination of claim 19, wherein each rotation of the conductor's curving path around the longitudinal axis of said housing constitutes one wind, and wherein said conductor is of a length to form at least two winds within said attenuator, the paths of each wind being parallel to produce a capacitative effect.

21. In combination:

first and second electrical conductor means for carrying an electrical firing signal from an electrical source to a firing means;

said conductor means passing through an attenuator means for attenuating electromagnetic energy and equalizing electrostatic energy;

said attenuator means being mounted within at least a portion of an electrically and thermally conductive housing having a top and a bottom, said attenuator means being in contact with said housing so as to dissipate thermal energy;

said attenuator means including an electrical ground element and being formed of an electrically conductive ferrite material in electrical contact with said ground element, said electrical conductor means being in electrical contact with said ferrite material, said ferrite material further having an electrical conductivity great enough that electrostatic energy induced in said electrical conductor means will be shunted through said ferrite material to said ground element, said ferrite material also having an electrical resistance great enough to prevent an electrical firing signal in said conductor means from being shunted to said ground element through said ferrite material;

said housing being formed of a material which will prevent the passage of electromagnetic energy therethrough;

a firing means having an input end electrically connected to said conductor means which is responsive to said electrical firing signal;

said housing enclosing said attenuator means and extending to the input end of said firing means, to shield said conductor means from said attenuator to said firing means; and said first conductor means being formed in spiral form within said attenuator and within said housing, said first conductor means formed in a three-dimensional curving path from top to bottom in said attenuator;

said second conductor means passing through said attenuator means and formed in a three dimensional spiral concentric to the first conductor means, such that said first and second conductors produce a capacitative effect between themselves.

22. In combination:

at least one electrical conductor means for carrying an electrical firing signal from an electrical source to a firing means;

said conductor means passing through an attenuator means for attenuating electromagnetic energy and equalizing electrostatic energy;

said attenuator means being mounted within at least a portion of a generally cylindrical housing having a top and bottom, said attenuator means being in contact with said housing so as to dissipate thermal energy;

said attenuator means including an electrical ground element and being formed of an electrically conductive ferrite material in electrical contact with said ground element, said electrical conductor means being in electrical contact with said ferrite material, said ferrite material further having an electrical conductivity great enough that electrostatic energy induced in said electrical conductor means will be shunted through said ferrite material to said ground element, said ferrite material also having an electrical resistance great enough to prevent an electrical firing signal in said conductor means from being shunted to said ground element through said ferrite material;

said housing being formed of a material which will prevent the passage of electromagnetic energy therethrough;

a firing means having an input end electrically connected to said conductor means which is responsive to said electrical firing signal;

said housing enclosing said attenuator means and extending to the input end of said firing means, to shield said conductor means from said attenuator to said firing means; and said conductor means being formed within said attenuator and within said housing with a plurality of portions parallel to one another so as to provide a capacitative effect in said conductor means between said parallel portions.

23. The combination of claim 22, wherein said parallel portions are oriented generally transversely to the longitudinal axis of said attenuator means.

24. The combination of claim 22, further comprising a second conductor passing through said attenuator means and formed with a plurality of portions parallel to one another and parallel to said parallel portions at said first conductor, so as to provide a capacitative effect in said conductor means between said parallel portions of said first and second condutors.

25. A squib, comprising:
a pyrotechnic charge;
electrical means for igniting said pyrotechnic charge, said electrical means including conductor means extending between and electrical source and said pyrotechnic charge;
attenuator means for dissipating electromagnetic energy and equalizing electrostatic energy induced in said conductor means, said attenuator means including an electrical ground element and being formed of an electrically conductive ferrite material in electrical contact with said ground element, said electrical conductor means being in electrical contact with said ferrite material, said ferrite material further having an electrical conductivity great enough that electrostatic energy induced in said electrical conductor means will be shunted through said ferrite material to said ground element, said ferrite material also having an electrical resistance great enough to prevent an electrical firing signal in said conductor means from being shunted to said ground element through said ferrite material;
a housing surrounding said attenuator and extending to said pyrotechnic charge;
said housing being formed of a material which will prevent passage of electromagnetic energy therethrough;
said conductor means passing through said ferrite material and terminating in said pyrotechnic charge;
an igniter means electrically connected between said conductor means to ignite said pyrotechnic charge upon passage of a firing signal therethrough.

* * * * *